United States Patent [19]

Nichols

[11] Patent Number: 5,047,536

[45] Date of Patent: Sep. 10, 1991

[54] HEXAHYDROBENZO(A)PHENANTHRIDINE COMPOUNDS

[75] Inventor: David E. Nichols, West Lafayette, Ind.

[73] Assignee: Purdue Research Foundation, West Lafayette, Ind.

[21] Appl. No.: 325,140

[22] Filed: Mar. 17, 1989

[51] Int. Cl.$^5$ .............................................. C07D 215/58
[52] U.S. Cl. ........................................ 546/61; 546/48
[58] Field of Search .................................. 546/48, 61

[56] References Cited

U.S. PATENT DOCUMENTS 3,912,740  10/1975  Zee-Cheng et al. .................. 546/48
3,939,165  2/1976   Schwan ................................ 546/61
4,737,503  4/1988   Sakamoto et al. ................... 514/279

OTHER PUBLICATIONS

Wei et al., Heterocycles, vol. 8, pp. 97-102 (1977).
Walker, G. N., Hypotensive Methoxyisoquinolones, JACS, vol. 76, p. 3999, 1954.
Laus, G., Tourwé, D., and Van Binst, G., Benzo and Indoloquinolizidine Derivatives[1] XIX, The Synthesis and Pharmacological Activity of Some Quinolizidine Derivatives, Analogues of Butaclamol, Heterocycles, vol. 22, No. 2, p. 311, 1984.
Riggs, R. M., Studies Directed Toward the Design of Specific Dopamine D-1/DA-1 Agonists and Antagonists, A Thesis Submitted to the Faculty of Purdue university-In Partial Fulfillment of the Requirements for the Degree of Doctor of Philosophy, 1986.

Primary Examiner—Mukund J. Shah
Assistant Examiner—E. C. Ward
Attorney, Agent, or Firm—Barnes & Thornburg

[57] ABSTRACT

Trans-hexahydrobenzophenanthridines of the formula

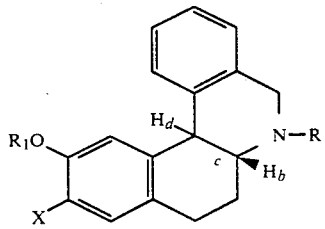

wherein R is hydrogen or $C_1$–$C_4$ alkyl; $R_1$ is hydrogen, benzoyl or pivaloyl; and x is hydrogen, chloro, bromo, iodo or a group of the formula $OR_2$, are novel ligands for dopamine receptors.

5 Claims, 1 Drawing Sheet

HEXAHYDROBENZO(A)PHENANTHRIDINE COMPOUNDS

FIELD OF INVENTION

This invention relates to novel ligands for dopamine receptors. More particularly this invention is directed to certain substituted trans-hexahydrobenzo[a]phenanthridine compounds useful as dopamine-like agents or as dopamine receptor blockers.

BACKGROUND AND SUMMARY OF THE INVENTION

Drugs with a dopamine-like action, or an ability to block (antagonize) dopamine receptors are of therapeutic interest for a variety of reasons. First, it is known that certain dopamine-like substances may have utility as agents to control hypertension. Recently, two compounds SKF 38393 and SKF 82526 (Fenoldopam) have been clinically evaluated by Smith-Kline laboratories as novel antihypertensives. Both of those compounds are dopamine-like agents that act specifically at dopamine D-1 receptors. Presently none of the marketed antihypertensive agents work by this mechanism, but there is a great interest by the pharmaceutical industry in evaluating agents of this type for treatment of high blood pressure.

Parkinson's disease is a chronic, progressive disease that primarily affects older patients. It is characterized by an inability to control the voluntary motor system, and by an inability to initiate voluntary movements. Currently it is treated by giving L-DOPA, a precursor for dopamine in the central nervous system. In the later stages of the disease, it is treated by administering dopamine-like agents such as bromocriptine (Parlodel) marketed by Sandoz pharmaceuticals.

Schizophrenia is a severe mental disorder where patients are unable to function in society without treatment. They have delusions, hallucinations, and thought disorders that affect their perceptions of reality. Currently, schizophrenia is treated with chlorpormazine (Thorazine) or haloperidol (Haldol). These drugs block the acute hallucinations and severe thought disorders of schizophrenia, but leave the intellect of treated patients "blunted". Additional side effects produced by those drugs include a drug-induced Parkinson's syndrome, where voluntary movement is inhibited, and a long-term side effect known as tardive dyskinesia, which includes facial tics and uncontrollable lip and tongue movements. Thorazine has been the most widely used anti-schizophrenic agent and has been in use for more than 25 years. Both Thorazine and Haldol are believed to act by occupying dopamine receptors of the D-2 classification, but they do not elicit a dopamine-like response. Instead, these drugs are dopamine D-2 receptor blocking agents, or antagonists. Recently there has been great interest in developing drugs that will block another type of dopamine receptor, the dopamine D-1 receptor subtype. Great excitement was generated by the discovery that a compound known as SCH 23390, developed by Schering-Plough pharmaceuticals, was a specific dopamine D-1 receptor blocker. However, clinical trials with that drug failed due to toxicity problems. Thus far, no company has been able to develop a dopamine D-1 specific antagonist for evaluation as an antipsychotic agent.

The present invention provides novel compounds, designated generally as substituted trans-5,6,6a,7, 8, 12b-hexahydrobenzo[a]phenanthridines. The biological activities of the present compounds range from potent dopamine-like activity affecting both D-1 and D-2 dopamine receptor subtypes to specific dopamine D-1 receptor antagonist activity. They can be administered by oral or parenteral routes of administration in amounts effective to produce, for example, anti-hypertensive, anti-Parkinson or anti-psychotic responses.

DETAILED DESCRIPTION OF THE INVENTION

Figure 1:
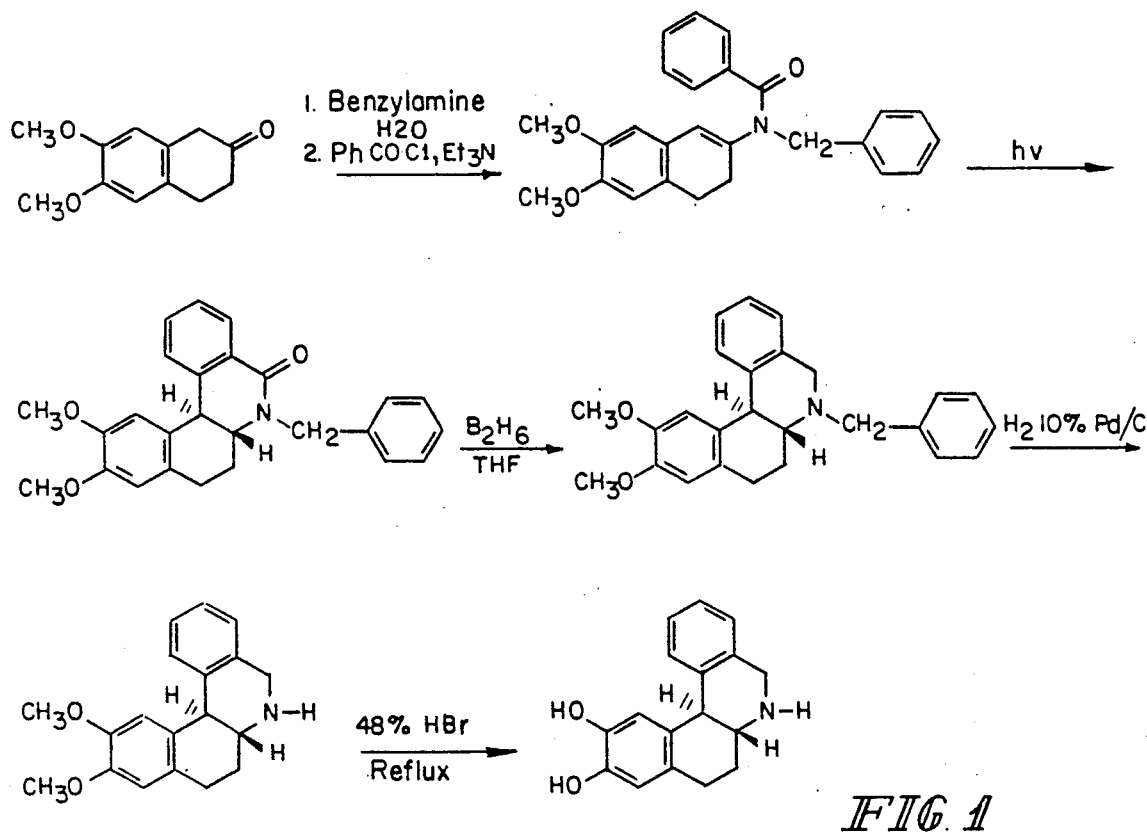
FIG. 1 illustrates the chemical conversions detailed in Example 1 for preparation of a compound of the present invention.

There is provided by this invention hexahydrobenzo[a]phenanthridine compounds of the general formula

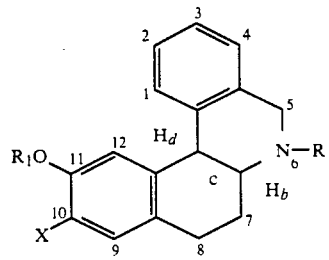

I wherein $H_a$ and $H_b$ are trans across ring fusion bond c, R is hydrogen or $C_1$–$C_4$ alkyl; $R_1$ is hydrogen, benzoyl or pivaloyl; and X is hydrogen, chloro, bromo, iodo or a group of the formula —$OR_2$ wherein $R_2$ is hydrogen, benzoyl or pivaloyl. In another embodiment of this invention when X is a group of the formula —$OR_2$ the groups $R_1$ and $R_2$ can be taken together to form a —$CH_2$— group, thus representing a methylenedioxy functional group bridging the C-10 and C-11 (see ring carbon numbering in Formula I) positions on the hexahydrobenzo[a]phenanthridine ring system.

Preferred compounds in accordance with this invention are represented by the formula

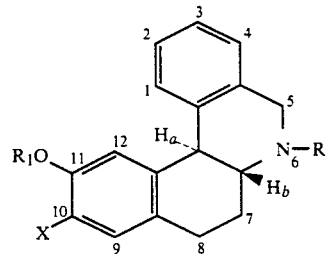

wherein R, $R_1$ and X are as defined above.

The term $C_1$–$C_4$ alkyl as used herein refers to methyl, ethyl, propyl, alkyl and cyclopropylmethyl. The selectivity of the present compounds for the dopamine D-1 and D-2 receptors are affected by the nature of the nitrogen substituent. Optimal dopamine D-1 agonist activity has been noted where R in Formula I or Formula II above is hydrogen or methyl.

N-Alkylation may be effected by a variety of methods, including, but not limited to, reductive animation of the compounds wherein R=H with an aldehyde and a reducing agent, treatment with an alkyl halide, treatment with a carboxylic acid in the presence of sodium borohydride, or treatment with carboxylic acid anhydrides followed by reduction, for example with lithium aluminum hydride or with borane.

All active compounds of the present invention bear an oxygen atom at the C-11 position as shown in Formulas I and II above. The C-10 unsubstituted, C-11 hydroxy compounds Possess dopamine D-1 antagonist, or weak agonist activity, depending on the alkyl group that is attached to the nitrogen atom. The most potent dopamine D-1 agonist compounds have a 10,11-dioxy substitution pattern, in particular, the 10,11-dihydroxy substituents. Compound potency and receptor selectivity in this series can be affected by the nature of the nitrogen substituent. The 10,11-dioxy substituents need not be in the form of hydroxyl groups. Masked hydroxyl groups, or prodrug (hydroxyl protecting) groups may also be used. For example, esterification of the 10,11-hydroxyl groups with, for example, benzoic acid or pivalic acid ester forming compounds (e.g., acid anhydrides) yield 10,11-dibenzoyl or dipivaloyl esters that are useful as prodrugs, i.e., they will be hydrolyzed in vivo to produce the biologically active 10,11-dihydroxy compound. A variety of biologically acceptable carboxylic acids may be used to accomplish this. Furthermore, the 10,11-dioxy ring substitution may be in the form of a 10,11-methylenedioxy group. In vivo, body metabolism will cleave this linkage to provide the more active 10,11-dihydroxy functionality.

Dopamine D-1 antagonists in accordance with this invention can bear a C-11 hydroxy with a halogen atom at the C-10 position, where the halogen atom can be bromo, chloro, or iodo. The iodo or bromo groups, for example, may also be a radioactive isotope, so that the resulting radioactive 10-halogen-11-hydroxy substituted compound can be used as a label in receptor binding studies.

While the bromination of the 11-hydroxy compound using elemental bromine has been illustrated in the examples, those skilled in the art may use a variety of halogenating conditions, employing either the 11-hydroxy or the 11-methoxy as substrates. Furthermore, the 11-oxy substituent compounds may also be nitrated in the C-10 position, followed by reduction to the amino compound, which can then also be transformed into a halo substituent via the diazonium salt.

The compounds of this invention can be formulated in conventional dosage forms for parenteral or oral administration. Preferred doses of the present compounds depend on many factors including the indication being treated, the route of administration and the overall condition of the patient. For oral administration effective doses of the present compounds are expected to range from about 0.5 mg/kg to about 50 mg/kg. Effective parenteral doses can range from about 0.1 to about 5 mg/kg.

EXAMPLES

Example 1. (See FIG. 1)

2 (N-benzyl-N-benzoyl)-6,7-dimethoxy-3,4-dihydro-2-napthylamine

To a solution of 4.50 g (21.8 mmol) of 6,7-dimethoxy-$\beta$-tetralone in 100 ml of toluene was added 2.46 g (23 mmol) of benzylamine. The reaction was heated at reflux overnight under $N_2$ with continuous water removal. The reaction was cooled, and the solvent was removed by rotary vacuum evaporation to yield the crude N-benzyl enamine as a brown oil.

This residue was dissolved in 80 ml of $CH_2Cl_2$, and to this was added 2.43 g (24 mmol) of triethylamine, and the solution was cooled in an ice bath. Benzoyl chloride (3.37 g, 24 mmol) was then dissolved in 15 ml of $CH_2Cl_2$ and this solution was then added dropwise to the cold stirring N-benzyl enamine solution. After complete addition the reaction was allowed to warm to room temperature and was left to stir overnight. The mixture was then washed successively with 2×50 ml of 5% aqueous HCl, 2×50 ml of 1 N NaOH, saturated NaCl solution, and was then dried over $MgSO_4$. After filtration, the filtrate was concentrated under vacuum. Crystallization from diethyl ether gave 5.6 g (64%) of the enamide, mp 109°–110° C. IR (KBr); 1620 cm/$^{-1}$; CIMS (isobutane); M+1 400; $^1$H-NMR (CDCl$_3$); $\delta$ 7.64 (m, 2, ArH), 7.33 (m, 8, ArH), 6.52 (s, 1, ArH), 6.38 (s, 1, ArH), 6.05 (s, 1, ArCH), 4.98 (s, 2, ArCH$_2$N), 3.80 (s, 3, OCH$_3$), 3.78 (s, 3, OCH$_3$), 2.47 (t, 2, CH$_2$, J=8.1 Hz), 2.11 (t, 2, Ch$_2$, J=8.1 Hz); Anal. (C$_{26}$H$_{25}$NO$_3$) C, H, N.

Trans-6-benzyl-10,11-dimethoxy-5,6,6a,7,8,12b-hexahydrobenzo [a]-phenanthridine-5-one A solution of 3.14 g (7.85 mmol) of the 6,7-dimethoxy enamide prepared above, in 300 ml of THF, was introduced into an Ace Glass 250 ml photochemical reactor. This solution was stirred while irradiating for 5 hours with a 450 watt Hanovia medium pressure, quartz, mercury-vapor lamp seated in a water cooled, quartz immersion well. The solution was concentrated in vacuo and crystallized from ether to provide 1.345 g (42.9%) of the 10,11-dimethoxy-lactam, mp 183°–186° C. IR (KBr); 1655, 1640 cm$^{-1}$; CIMS (isobutane); M+1 400; $^1$H-NMR (CDCl$_3$); $\delta$ 8.19 (m, 1 ArH), 7.52 (m, 1, ArH), 7.46 (m, 2, ArH), 7.26 (m, 5, ArH), 6.92 (s, 1, ArH), 6.63 (s, 1, ArH), 5.35 (d, 1, ArCH$_2$N, J=16.0 Hz), 4.78 (d, 1, ArCH$_2$N, J=16.0 Hz), 4.37 (d, 1, Ar$_2$CH, J=11.3 Hz), 3.89 (s, 3, OCH$_3$), 3.88 (s, 3, OCH$_3$), 3.80 (m, 1 CHN), 2.67 (m, 2, ArCH$_2$), 2.25 (m, 1, CH$_2$CN), 1.75 (m, 1, CH$_2$CN), Anal. (C$_{26}$H$_{25}$NO$_3$) C, H, N.

Trans 6-benzyl 10,11-dimethoxy-5,6,6a,7,8,12b-hexahydrobenzo [a]phenanthridine hydrochloride A solution of 1.20 g (3 mmol) of the lactam prepared above, in 100 ml of dry THF was cooled in an ice-salt bath and 6.0 ml of 1 molar solution of BH$_3$ was added via syringe. The reaction was heated at reflux overnight. Water (10 ml) was added dropwise, and the reaction mixture was concentrated by distillation at atmospheric pressure. The residue was stirred with 50 ml of toluene, 1.0 ml of methane sulfonic acid was added, and the mixture was heated with stirring on the steam bath for one hour. The mixture was diluted with 40 ml of water and the aqueous layer was separated. The toluene was extracted several times with water, and the aqueous layers were combined. After basification of the aqueous phase with conc. ammonium hydroxide, the free base was extracted into 5×25 ml of CH$_2$Cl$_2$. This organic extract was washed with satd NaCl solution, and dried over MgSO$_4$. After filtration, the organic solution was concentrated under vacuum, the residue was taken up into ethanol, and carefully acidified with conc HCl. After drying several times by azeotropic distillation of ethanol, the product was crystallized from ethanol to afford 0.97 g (76.5%) of the salt, mp 235°–237° C. CIMS (NH$_3$); M+1 386; $^1$H-NMR (CDCl$_3$, free base); δ 7.37 (m, 9 ArH), 6.89 (s, 1, ArH), 6.74 (s, 1, ArH) 4.07 (d, 1, Ar$_2$CH, J=10.7 (Hz), 3.90 (s, 3, OCH$_3$) 3.82 (m, 2, ArCH$_2$N), 3.79 (s, 3, OCH$_3$), 3.52 (d, 1 ArCH$_2$N, J=15.3 Hz), 3.30 (d, 1, ArCH$_2$), J=13.1 Hz), 2.86 (m, 2, CHN, ArCH$_2$), 2.30 (m, 2, ArCH$_2$, CH$_2$CN), 1.95 (m, 1, CH$_2$CN).

Trans 10,11-dimethoxy-5,6,6a,7,8,12b-hexahydrobenzo [a]phenanthridine hydrochloride A solution of 0.201 g (.48 mmol) of the 6-benzyl hydrochloride salt prepared above in 50 ml of 95% ethanol containing 50 mg of 10% Pd-C catalyst was shaken at room temperature under 50 psig of H$_2$ for 8 hours. After removal of the catalyst by filtration, the solution was concentrated to dryness under vacuum and the residue was recrystallized from acetonitrile to afford 0.119 g (75%) of crystalline salt, mp 243°–244° C. CIMS (NH$_3$); M+1 296; $^1$H-NMR (CDCl$_3$, free base); δ 7.46 (d, 1, ArH, J=6.1 Hz), 7.24 (m, 3, ArH), 6.91 (s, 1, ArH), 6.74 (s, 1, ArH), 4.09 (s, 2, ArCH$_2$N), 3.88 (s, 3, OCH$_3$), 3.78 (m, 4, OCH$_3$, Ar$_2$CH), 2.87 (m, 3, CHN, ArCH$_2$), 2.17 (m, 1, CH$_2$CN), 1.61 (m, 2, NH, CH$_2$CN).

Trans-10,11-dihydroxy-5,6,6a,7,8,12b-hexahydrobenzo [a]phenanthridine hydrochloride A suspension of 0.109 g (0.33 mmol) of the 0,0-dimethyl salt obtained from the reduction above, in 1.5 ml of 48% HBr, was heated at reflux, under N$_2$, for 3 hours. The reaction mixture was concentrated to dryness under high vacuum. This material was dissolved in water and neutralized to the free base with NaHCO$_3$, while cooling the solution in an ice bath. The free base was extracted into chloroform, dried, filtered and concentrated in vacuo. The residue was dissolved in ethanol and carefully neutralized with conc. HCl. After removal of the volatiles, the salt was crystallized as a solvate from methanol. This afforded 30 mg (25.2%) of the desired salt, solvated with a stoichiometry of 1 molecule of amine salt and 1.8 molecules of CH$_3$OH, as pale yellow crystals, mp 195° C. CIMS (isobutane); M+1 268; $^1$H-NMR (DMSO, HBr salt); δ 9.40 (bs, 1, $^+$NH$_2$), 9.22 (bs, 1, $^+$NH$_2$), 8.76 (bs, 2, OH), 7.38 (m, 4, ArH), 6.72 (s, 1, ArH), 6.63 (s, 1, ArH), 4.40 (s, 2, ArCH$_2$N$^+$), 4.16 (d, 1, Ar$_2$CH, J=11.1 Hz), 3.00 (m, 1, CHN$^+$), 2.75 (m, 2, ArCH$_2$), 2.17 (m, 1, CH$_2$CN$^+$), 1.90 (m, 1, CH$_2$CN$^+$).

Example 2

By a similar series of reactions, 7-methoxy-β-tetralone was converted into Trans-11-methoxy-5,6,6a,7,8,12b-hexahydrobenzo[a]phenanthridine. Some of the reaction methods are described in detail; in cases where the procedures were identical, only the analytical data are provided.

2-(N-Benzoyl-N-benzyl)-7-methoxy-3,4-dihydro-2-naphthylamine

A solution of 20.0 g (0.113 mol) of 7-methoxy-β-tetralone and 12.77 g (0.119 mol) benzylamine in 250 ml of benzene was heated under N$_2$ for 3 hours in an oil bath at 100° C. with continuous water removal, at which point 2.0 ml water had been collected. The heat was removed and the mixture was concentrated in vacuo, providing a brown oil.

The crude enamine was dissolved in 500 ml CH$_2$Cl$_2$, 12.3 g (120 mmol) of triethylamine was added, and the mixture was cooled under N$_2$ and in an ice water bath. This was followed by the addition of 17.15 g (0.12 mol) of benzoyl chloride, in 2 ml aliquots. The solution was allowed to come to room temperature while stirring overnight. The reaction mixture was washed with 2×50 ml of 5% HCl, 2×50 ml of 1 N NaOH, and water, then dried (MgSO$_4$) and filtered through a silica gel plug and Celite. Concentration in vacuo yielded a foam which was then crystallized from ether, which was collected by filtration to provide 24.83 g (59.2%) of enamide, mp 94.5°–95.5° C. Another 10.22 g of product was obtained by crystallization of the filtrate for a total yield of 83.6%. IR (KBr); 1620 cm$^{-1}$; CIMS (isobutane); M+1 370; $^1$H-NMR (CDCl$_3$); δ 7.62 (m, 2, ArH), 7.33 (m, 8, ArH), 6.88 (d, 1, ArH, J=8.0 Hz) 6.60 (dd, 1, ArH, J=8.0 Hz, J=2.7 Hz), 6.40 (d, 1, ArH, J=2.7 Hz), 6.10 (s, 1, ArCH), 5.00 (s, 2, ArCH$_2$N), 3.71 (s, 3, OCH$_3$), 2.48 (t, 2, CH$_2$, J=7.9 Hz), 2.11 (t, 2, CH$_2$, J=7.9 Hz); Anal. (C$_{25}$H$_{23}$NO$_2$) C, H, N.

Trans-6-benzyl-11-methoxy-5,6,6a,7,8,12b-hexahydrobenzo [a]phenanthridine-5-one

A solution of 24.321 g (65.8 mmol) of the 7-methoxy-enamide prepared above in 300 ml of THF was introduced into an Ace Glass 250 ml photochemical reactor. This solution was stirred while irradiating for 10 hours with a 450 watt Hanovia medium pressure, quartz, mercury-vapor lamp seated in a water cooled, quartz immersion well. The solution was concentration in vacuo and crystallized from ether to provide 16.97 g (69.8%) of the 11-methoxy-lactam, mp 128°–129° C. IR (KBr); 1650, 1630 cm$^{-1}$; CIMS (isobutane); M+1 370; $^1$H-NMR (CDCl$_3$); δ 8.19 (m, 1 ArH), 7.55 (m, 1, ArH), 7.46 (m, 2, ArH), 7.27 (m, 5, ArH), 7.08 (d, 1, ArH, J=8.6 Hz), 6.98 (d, 1, ArH, J=2.4 Hz), 6.80 (dd, 1, ArH, J=8.6 Hz, J=2.4 Hz), 5.34 (d, 1, ArCH$_2$N, J=16.1 Hz), 4.80 (d, 1, ArCH$_2$N, J=16.1 Hz), 4.40 (d, 1, Ar$_2$CH, J=11.3 Hz), 3.83 (m, 4, OCH$_3$, CHN), 2.70 (m, 2, ArCH$_2$), 2.27 (m, 1, CH$_2$CN), 1.74 (m, 1, CH$_2$CN), Anal. (C$_{26}$H$_{25}$NO$_3$) C, H, N.

Trans 11-Methoxy-6-benzyl-5,6,6a,7,8,12b-hexahydrobenzo [a]phenanthridine hydrochloride As described in Example 1, the lactam prepared above was reduced with diborane and isolated to afford typical yields of 85-90%. Melting pts.: free base 118°–120° C., HCl Salt 205°–208° C. (recrystallized from ethanol). CIMS (NH$_3$): M+1 356. $^1$H-NMR (CDCl$_3$, free base); δ 7.34 (m, 10, ArH), 6.88 (d, 1, ArH, J=2.5 Hz), 6.72 (dd, 1, ArH, J=8.3 Hz, J=2.5 Hz), 4.10 (d, 1, Ar$_2$CH, J=10.7 Hz), 3.96 (d, 1, ArCH$_2$N, J=13.1 Hz), 3.78 (d, 1, ArCH$_2$N, J=15.2 Hz), 3.72 (s, 3, OCH$_3$), 3.47 (d, 1, ArCH$_2$N, J=15.2 Hz), 3.28 (d, 1, ArCH$_2$N, J=13.1 Hz), 2.91 (m, 2, ArCH$_2$, CHN), 2.40 (m, 1, ArCH$_2$), 2.20 (m, 1, CH$_2$CN), 2.00 (m, 1, CH$_2$CN). Anal. (C$_{25}$H$_{26}$ClNO) C, H, Cl, N.

Trans-11-Methoxy-5,6,6a,7,8,12b-hexahydrobenzo [a]phenanthridine hydrochloride

As described in Example 1, the 6-benzyl amine hydrochloride prepared above was reduced catalytically at 50 psig H$_2$ in ethanol over 10% Pd-C catalyst, to afford typical yields of 75-95%. Melting point: HCl Salt 233° C., (recrystallized from ethanol). CIMS (NH$_3$): M+1 266; $^1$H-NMR (CDCl$_3$, HCl Salt); δ 7.45 (d, 1, ArH, J=4.3 Hz), 7.34 (m, 3, ArH), 7.14 (d, 1, ArH, J=7.8 Hz), 6.92 (d, 1, ArH, J=2.7 Hz); 6.80 (dd, 1, ArH, J=7.8 Hz, J=2.7 Hz), 4.45 (m, 3, ArCH$_2$N+, Ar$_2$CH), 3.80 (s, 3, OCH$_3$), 3.10 (m, 1, CHN+), 2.90 (m, 2, ArCH$_2$), 2.51 (m, 1, CH$_2$CN+) 2.39 (m, 1, CH$_2$CN+), Anal. (C$_{18}$H$_{20}$ClNO) C, H, Cl, N.

Figure 2:
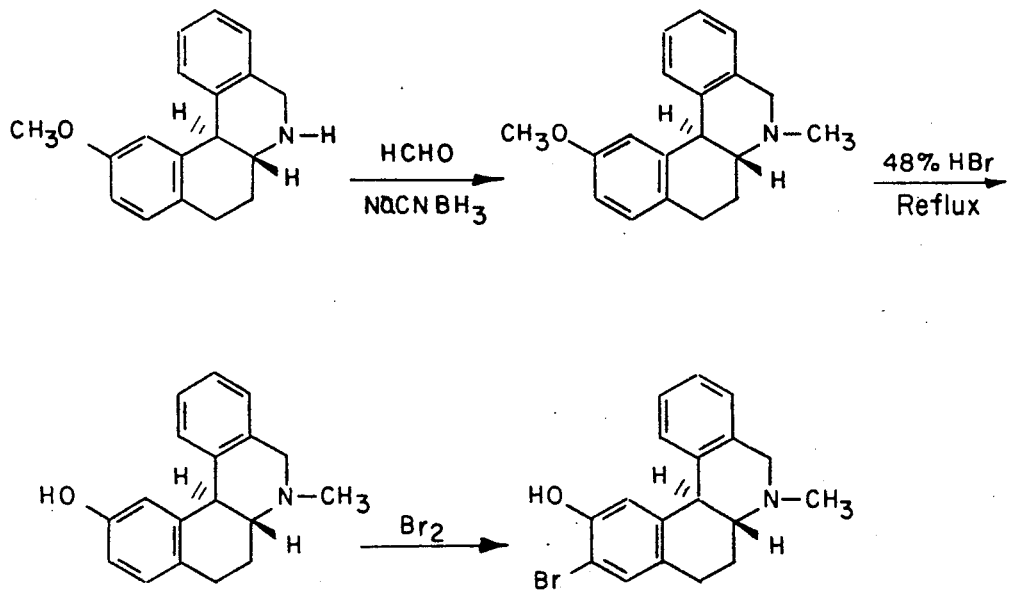
FIG. 2 illustrates chemical conversions detailed in Example 2 for preparation of compounds of the present invention.

Trans-11-methoxy-6-methyl-5,6,6a,7,8,12b-hexahydrobenzo [a]phenanthridine hydrochloride (See FIG. 2) To a solution of 1.081 g (3.42 mmol of 11-methoxy-hexahydrobenzo[a]phenanthridine hydrochloride in 30 ml of methanol was added 1.85 ml (66.8 mmol) of 37% formalin solution, followed by 0.93 g (14.8 mmol) of NaCNBH$_3$. After stirring at room temperature overnight, the volatiles were removed in vacuo, the residue was diluted with 50 ml of 2N HCl, stirred for 45 min. and washed with 3×15 ml of diethyl ether. The aqueous fraction was made basic with NaOH pellets and then extracted with 3×30 ml CH$_2$Cl$_2$. The combined dichloromethane fractions were dried (MgSO$_4$), filtered and concentrated in vacuo to give 1.02 g (100%) of the free base as a colorless oil. The oil was dissolved in abs. ethanol, acidified with conc. HCl, dried by azeotropic distillation of ethanol, and was then crystallized from absolute ethanol. This provided 0.947 g (84%) of the amine hydrochloride, mp 215°–218° C. CIMS (NH$_3$): M+1 280; $^1$H-NMR (CDCl$_3$, free base); δ 7.40 (d, 1, ArH, J=7 Hz), 7.24 (m, 2, ArH), 7.13 (m, 2, ArH), 6.81 (d, 1, ArH, J=2.7 Hz); 6.72 (dd, 1, ArH, J=8 Hz, J=2.7 Hz), 4.02 (d, 1, Ar$_2$CH, J=9.9 Hz), 3.84 (d, 1, ArCH$_2$N, J=15.0 Hz), 3.72 (s, 3, OCH$_3$), 3.50 (d, 1, ArCH$_2$N, J=15.0 Hz), 2.89 (m, 2, ArCH$_2$, CHN) 2.39 (s, 3, NCH$_3$), 2.08 (m, 2, ArCH$_2$, CH$_2$CN), 1.92 (m, 1, CH$_2$CN).

Trans-6-methyl-11-hydroxy-5,6,6a,7,8,12b-hexahydrobenzo [a]phenanthridine hydrobromide (See FIG. 2) A suspension of 0.456 g. (1.44 mmol) of 11-methoxy-6-methyl-hexahydrobenzo[a]phenanthridine hydrochloride in 10 ml 48% HBr was heated for 2.5 hours at reflux under N$_2$ in an oil bath. The heat was removed, and the reaction mixture was placed in the refrigerator overnight. The white precipitate was collected by suction filtration, and after washing the crystals on the filter with cold ethanol and ether, the product weighed 403 mg (80.6%), mp 251°–254° C. The filtrate was concentrated and the residue was crystallized from ethanol to provide additional product, giving essentially a quantitative total yield of the phenol, mp 254° C. CIMS (NH$_3$): M+1 266; $^1$H-NMR (CDCl$_3$, free base); δ 7.38 (d, 1, ArH, J=7.5 Hz), 7.22 (m, 3, ArH), 7.04 (d, 1, ArH, J=8.2 Hz), 6.69 (s, 1, ArH); 6.64 (d, 1, ArH, J=8.2 Hz,) 3.98 (d, 1, Ar$_2$CH), 3.84 (d, 1, ArCH$_2$N, J=14.5 Hz), 3.50 (d, 1, ArCH$_2$N, J=14.5 Hz), 2.87 (m, 2, CH$_2$ and CHN) 2.38 (s, 3, NCH$_3$), 2.09 (m, 2, CH), 1.86 (m, 1, CH$_2$CN).

Trans-6-methyl-10-bromo-11-hydroxy-5,6,6a,7,8,12b-hexahydrobenzo[a]phenanthridine hydrobromide (See FIG. 2) A solution of 0.300 g (0.866 mol) of 11-hydroxy-6-methyl-hexahydrobenzo[a]phenanthridine hydrobromide in 100 ml water was made basic with conc. NH$_4$OH. The precipitate was removed by suction filtration, washed with water and dried to provide 0.23 g (100%) of the free base. This was dissolved in 100 ml of glacial acetic acid under N$_2$, and the solution was cooled to 10° C. with a water bath. To this was added 53 ml of a 16.455 millimolar solution of Br$_2$ in glacial acetic acid (0.872 mmol Br$_2$), with stirring. The solution was allowed to warm to room temperature and was stirred overnight. The brominated compound precipitated and was removed by suction filtration and was washed on the filter with ether. The pale off-white solid weighed 0.165 g (44.8%), mp 270° C. Recrystalliation from methanol provided an analytical sample, mp 275°–277° C. CIMS (NH$_3$): M+1 344, 346; $^1$H-NMR (CDCl$_3$, free base); 7.19 (m, 5, ArH), 6.88 (s, 1, ArH), 3.94 (d, 1, Ar$_2$CH, J=9.5 Hz), 3.86 (d, 1, ArCH$_2$N, J.=16.3 Hz), 3.50 (s, 1, ArCH$_2$N, J=16.3 Hz), 2.80 (m, 2, ArCH, CHN) 2.38 (s, 3, NCH$_3$), 2.07 (m, 3, ArCH, CH$_2$CN). Anal. (C$_{18}$H$_{19}$BrClNO): C, H, N.

I claim:

1. A compound of the formula

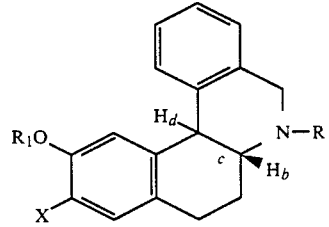

wherein H$_a$ and H$_b$ are trans across ring fusion bond c;
R is hydrogen or C$_1$–C$_4$ alkyl;
R$_1$ is hydrogen, benzoyl or pivaloyl;
X is hydrogen, chloro, bromo, iodo or a group of the formula —OR$_2$ wherein R$_2$ is hydrogen, benzoyl or pivaloyl, provided that when X is a group of the formula OR$_2$, the groups R$_1$ and R$_2$ can be taken together to form a group of the formula —CH$_2$—.

2. The compound of claim 1 of the formula

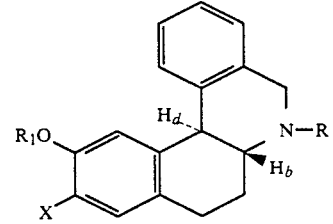

3. The compound of claim 2 wherein X is a group of the formula —OR$_2$ and R, R$_1$ and R$_2$ are each hydrogen.

4. The compound of claim 2 wherein R is methyl, R$_1$ is hydrogen, and X is bromo.

5. The compound of claim 2 wherein R is methyl, R$_1$ is hydrogen and X is hydrogen.

* * * * *

UNITED STATES PATENT AND TRADEMARK OFFICE
CERTIFICATE OF CORRECTION

PATENT NO.  : 5,047,536

DATED       : September 10, 1991

INVENTOR(S) : David E. Nichols

It is certified that error appears in the above-identified patent and that said Letters Patent is hereby corrected as shown below:

On the title page, in item [57] ABSTRACT:
Please replace the structural formula in the Abstract with the following correct formula:

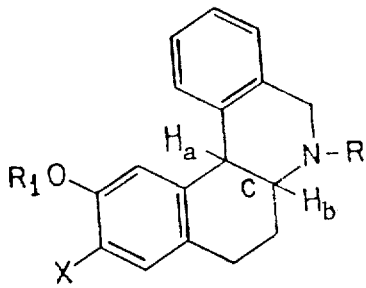

Please replace the structural formula at Column 2, lines 25-35 with the following correct formula:

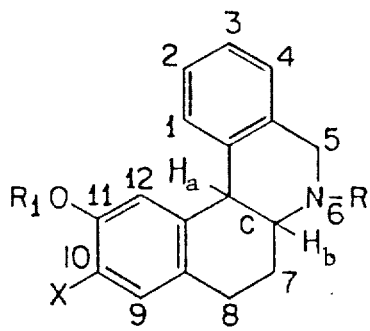

Column 3, line 12, "Possess" should read -- possess --.

UNITED STATES PATENT AND TRADEMARK OFFICE
CERTIFICATE OF CORRECTION

PATENT NO.  :  5,047,536

DATED       :  September 10, 1991

INVENTOR(S) :  David E. Nichols

It is certified that error appears in the above-identified patent and that said Letters Patent is hereby corrected as shown below:

Column 8, lines 25-33:
Please replace the structural formula in claim 1 with the following correct formula:

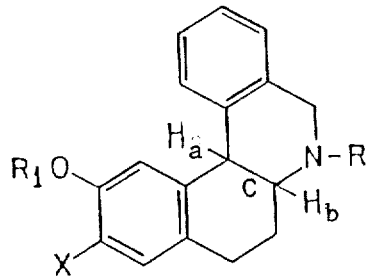

UNITED STATES PATENT AND TRADEMARK OFFICE
CERTIFICATE OF CORRECTION

PATENT NO. : 5,047,536

DATED : September 10, 1991

INVENTOR(S) : Favid E. Nichols

It is certified that error appears in the above-identified patent and that said Letters Patent is hereby corrected as shown below:

Column 8, lines 45-53:
   Please replace the structural formula in claim 2 with the following correct formula:

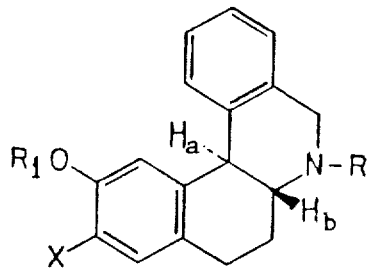

Signed and Sealed this

Sixth Day of July, 1993

*Attest:*

MICHAEL K. KIRK

*Attesting Officer*   Acting Commissioner of Patents and Trademarks

UNITED STATES PATENT AND TRADEMARK OFFICE
CERTIFICATE OF CORRECTION

PATENT NO. : 5,047,536
DATED : September 10, 1991
INVENTOR(S) : David E. Nichols It is certified that error appears in the above-indentified patent and that said Letters Patent is hereby corrected as shown below:

add at column 1, line 4 the following:

-- This invention was made with Government support under Grant #L-31106 awarded by the National Institutes of Health. The Government has certain rights in the invention.--.

Signed and Sealed this

Eighteenth Day of June, 1996

Attest:

BRUCE LEHMAN

Attesting Officer

Commissioner of Patents and Trademarks